US006602399B1

(12) United States Patent
Fromherz et al.

(10) Patent No.: US 6,602,399 B1
(45) Date of Patent: Aug. 5, 2003

(54) SIGNAL RECORDING OF A RECEPTOR-EFFECTOR-SYSTEM BY AN EXTRACELLULAR PLANAR POTENTIAL-SENSITIVE ELECTRODE

(75) Inventors: Peter Fromherz, München (DE); Elisabeth Meyer, München (DE); Bernhard Straub, München (DE)

(73) Assignee: Max-Planck-Gesellschaft zur Forderung der Wissenchaften e.V. (DE)

( * ) Notice: Subject to any disclaimer, the term of this patent is extended or adjusted under 35 U.S.C. 154(b) by 0 days.

(21) Appl. No.: 09/532,871

(22) Filed: Mar. 22, 2000

(51) Int. Cl.$^7$ ............................................. G01N 27/327
(52) U.S. Cl. ................. 205/777.5; 204/403.01
(58) Field of Search ................... 204/403, 403.01; 435/4; 436/149; 422/82.01, 82.02; 205/777.5

(56) References Cited

U.S. PATENT DOCUMENTS 6,051,422 A * 4/2000 Kovacs et al. ........... 435/287.1
6,280,586 B1 * 8/2001 Wolf et al. ................. 204/403

FOREIGN PATENT DOCUMENTS

EP      0 773 292 A1    5/1997

OTHER PUBLICATIONS

P. 1 of "Voltage measurement" entry in the McGraw–Hill "Online Encyclopedia of Science & Technology", accessed Nov. 26, 2002.*
Schätzthauer, R. et al. "Neuron–silicon junction with voltage–gated ionic currents", European Journal of Neuroscience, vol. 10 (1998); pp. 1956–1962.
Vassanelli, S. et al. "Neurons from rat brain coupled to transistors", Applied Physics A, vol. 65 (1997); pp. 85–88.
Fromherz, P. et al. "A Neuron–Silicon Junction: A Retzius Cell of the Leech on an Insulated–Gate Field–Effect Transistor", Science, American Association for the Advancement of Science, US, vol. 252, May 31, 1991, pp. 1290–1293.
Vassanelli, S. et al. "Transistor records of excitable neurons from rat brain", Applied Physics A, vol. 66 (1998), pp. 459–463.
Vassanelli, S. et al. "Transistor Probes Local Potassium Conductances in the Adhesion Region of Cultured Rat Hippocampal Neurons", Journal of Neuroscience, vol. 19(16) (1999), pp. 6767–6773.
Straub, B. et al. "Recombinant maxi–K channels on transistor, a prototype of iono–electronic interfacing", Nature Biotechnology, vol. 19(2) (Feb. 2001), pp. 121–124.
Straub, B. et al. "Accumulation of Recombinant Potassium Channels in Cell Adhesion Probed by Transistor", Society for Neuroscience Abstracts, vol. 26(1–2) (2000), pages Abstract No. –337.18, XP002210084.

* cited by examiner

Primary Examiner—Nam Nguyen
Assistant Examiner—Alex Noguerola
(74) Attorney, Agent, or Firm—Rothwell, Figg, Ernst & Manbeck

(57) ABSTRACT

The present invention relates to bioelectronic devices comprising living cells which are in operative contact with an extracellular planar potential-sensitive electrode, e.g. a field effect transistor. The cells comprise an ion channel/receptor system which is responsive to stimuli. Thus, the device is suitable as a bioelectronic sensor. The electrode may also have a capacitive stimulating spot, with which the electrical or functional state of the cell or its ion channel/receptor system may be affected.

28 Claims, 3 Drawing Sheets

Figure 1A:
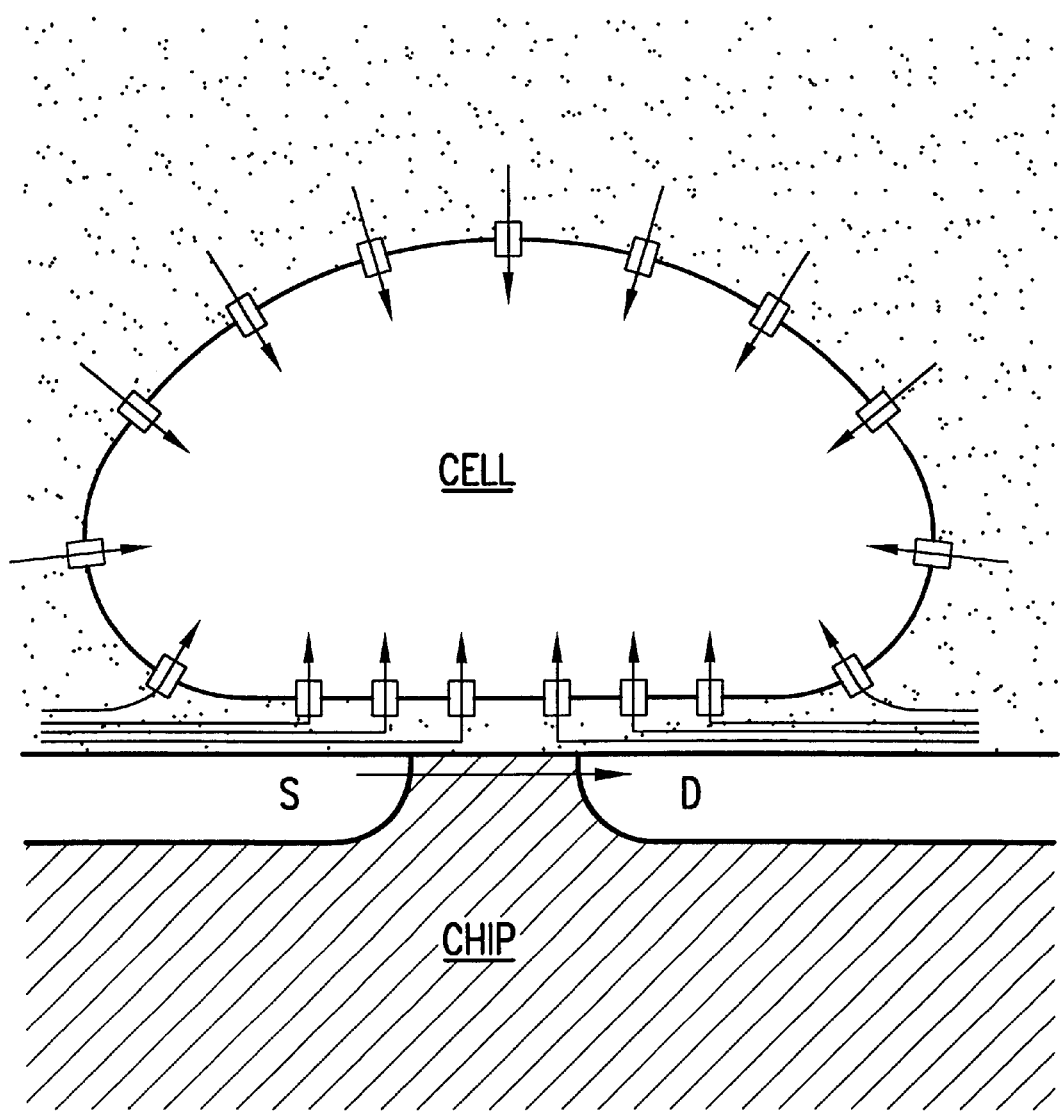

SIGNAL RECORDING OF A RECEPTOR-EFFECTOR-SYSTEM BY AN EXTRACELLULAR PLANAR POTENTIAL-SENSITIVE ELECTRODE

DESCRIPTION

The present invention relates to biolelectronic devices comprising living cells which are in operative contact with an extracellular planar potential-sensitive electrode, e.g. a field effect transistor. The cells comprise an ion channel/receptor system which is responsive to stimuli. Thus, the device is suitable as a bioelectronic sensor. The electode may also have a capacitive stimulating spot, with which the electrical or functional state of the cell or its ion channel/receptor system may be affected.

To determine the pharmaceutical effect of test substances, often so-called cellular screening assays are performed in which a cell to be tested containing a receptor system is brought into contact with a test substance in order to examine its function as an effector on the cellular receptor system. These test procedures are often complicated and expensive. Thus, there is a need for devices and methods which allow a quick and efficient screening of many cells. These could simplify the procedure of pharmaceutical tests.

According to the present invention, this problem is solved by combining receptor-effector systems with the functional characteristics of ion channels. The activity of these ion channels is modulated due to the effect of the receptor-effector system. This modulation can be detected by an extracellular planar potential sensitive electrode.

Thus, a subject matter of the present invention is bioelectronic device comprising a) a cell which expresses an ion channel/receptor system wherein said ion channel is responsive to a change in the functional and/or conformational characteristics of the receptor and b) an extracellular planar potential-sensitive electrode wherein the cell is in operative contact with said electrode.

The device of the present invention comprises a living cell. This cell may be a microorganism, e.g. a bacterial cell or a yeast or fungal cell. Preferably, however, the cell is a eukaryotic cell, more preferably, a mammalian cell. Further, it is preferred that the cell overexpresses the ion channel/receptor system, i.e. the cell is manipulated, e.g. by genetic engineering or mutation in a way that components of the ion channel/receptor system are expressed in a higher amount than in a comparative untreated cell. More preferably, the cell is transfected with nucleic acid molecules encoding components of the ion channel/receptor system. In this embodiment of the invention the cell comprises heterologous nucleic molecules which encode at least a part of the components of the ion channel/receptor system and which allow overexpression of said components.

The ion channel/receptor system comprises a polypeptide or a plurality of polypeptides. On the one hand, the ion channel/receptor system comprises an ion channel component, e.g. a polypeptide or a plurality of polypeptides being capable of mediating an ion, i.e. cation and/or anion current through a cell membrane. On the other hand, the ion channel/receptor system comprises a receptor component which is responsive to stimuli. The receptor may be the ion channel or a part of the ion channel. The receptor, however, may be a molecule which is different from the ion channel, which is, however, in operative connection with the ion channel, e.g. a change in the functional and/or conformational state of the receptor results in a change of the functional state of the ion channel thus resulting in a detectable change of ion current through the cell membrane. The stimuli by which the receptor may be mediated are preferably selected from changes in the potential (inside or outside the cell), the presence or absence of effectors, e.g. ligands of the receptor, illumination, mechanical stimulation, stimulation by stimulation spots on the electrode or combinations thereof.

The cell is cultivated on a planar potential-sensitive electrode. Methods of cultivating cells on planar potential-sensitive electrodes are disclosed e.g. in S. Vassanelli, P. Fromherz "Neurons from Rat Brain Coupled to Transistors" Appl. Phys. A 65, 85–88 (1997). By means of these cultivation cells are obtained, which grow on the potential-sensitive regions of the electrode resulting in an operative contact of the cell and the electrode.

The functional characteristics of the ion channels in the cell include an opening of the channels which will cause an ion current through all participating channels. These ion currents will also flow in the region of operative contact between cell and electrode resulting in a detectable signal which can be measured by the extracellular planar potential-sensitive electrode. The detectable signal may be e.g. a voltage drop due to a junction resistance by the narrow cleft between cell and substrate or the change of the surface potential of the electrode due to diffuse ion concentration changes in the operative contact zone.

A change in functional characteristics e.g. conductivity of the ion channel changes the ion current and therefore the electrical signal detected by the electrode. Since the ion channels are responsive to the effector-receptor system, an alteration in the effector-receptor system will modulate the opening of the ion channels and thus result in a detectable signal.

Ion channels, particularly the gating characteristics thereof, can be modulated by different methods, e.g. by voltage modulation across the membrane (voltage-gated ion channels), by ligands acting on the intracellular and/or extracellular side of the channel (ligand-gated ion channels), by mechanical changes (mechanically-gated ion channels) or by combinations thereof.

Voltage-gated ion channels, i.e. ion channels which are voltage sensitive, will change their conductivity with the potential drop over the membrane ($V_m = V_{intra} - V_{extra}$). If the electrolyte, i.e. the culture medium in which the cell is grown, is grounded ($V_{extra} = 0$ mV) this potential drop equals the intracellular membrane ($V_m = V_{intra}$). This potential drop may be measured and/or modulated by patch clamp devices, i.e. electrodes which are inserted in or attached to the cell, and allow an adjustment of $V_m$ to a fixed potential. In another embodiment, the conductivity of voltage-gated ion channels may be changed by voltage modulation due to an interaction with other ion channels, e.g. by means of an action potential. $V_m$ is changed due to ion currents flowing into a cell through different ion channels. This co-operation of several ion channels influences the potential drop over the membrane leading in some cases to an action potential. Moreover, the potential difference between intracellular and extracellular side of the membrane may be modulated by using stimulation spots on the electrode.

A stimulation spot may be integrated next to the potential-sensitive electrode being in operative contact to the cell (Stett et al., Phys. Rev. E 55 (1997), 85). Thus, a device with the features of stimulation and recording may be built. A stimulation spot can, e.g. trigger an action potential which then will be recorded by the extracellular electrode.

Ligands can modulate ion channels preferably by two mechanisms, ionotropic and second messenger systems. In an ionotropic system the ligand molecules bind directly to the ion channels and alter their gating characteristics, e.g. intracellular $Ca^{2+}$ shifts the gating curve of some $K^+$ channels (DiChiara and Reinhard, J. Physiol. 489.2 (1995), 403). In second messenger systems the ligand molecules bind to a receptor which will first trigger some other molecules before the ion channel is influenced, e.g. many glutamate-second messenger systems.

Of course these different methods of modulating ion channels may be combined to create an effective biosensor which may be used for assaying the influence of a change in environmental parameters, e.g. a test substance (effector) on a receptor molecule in the cell.

The coupling of several ion channels may lead to a sudden and specific voltage drop over the membrane of the cell, called an action potential. To release an action potential there are at least two types of channels necessary, e.g. potassium and sodium channels. Both types of channels can be transfected into cells. Alternatively, one may use cell types which already have intrinsic receptors and respond with an action potential, e.g. chromaffin cells or nerve cells. To trigger an action potential one may use one or several of the techniques described above.

The combination of ion channels with the ability to release an action potential and a receptor-effector system is a powerful tool. The advantage of an action potential is the fast and large voltage drop over the membrane which can easily be detected with an extracellular electrode as an "event". If the signal is very weak, one may use techniques of averaging. Thus, a simple and uncomplicated device and method for assaying substances, if they influence the release of action potentials, is provided.

In a further embodiment of the invention caged probes may be used for a quick release of a large amount of a ligand. Biologically active substances, e.g. $Ca^{2+}$ or the neurotransmitter L-glutamate may be released by UV-illumination, UV-lasers or flashlamps, and act on the receptor.

A specific example of a device according to the present invention are cells which are transfected with the α- and β-subunits of the voltage-dependent potassium channel hSlo. These cells are cultivated on a field-effect transistor. The characteristic gating curve of the ion channel may be shifted by β-estradiol (Valverde et al., Science 285 (1999), 1929). This shift corresponds to the opening of ion channels. By changing the extracellular concentration of β-estradiol an ion current will flow and can be detected by the field-effect-transistor under the cells. This system may be used as a sensor for β-estradiol concentration.

In another preferred embodiment cells are transfected with a nucleic acid encoding an ionotropic receptor for glutamate, e.g. the NMDA receptor. The ionic flux through the receptor consists of potassium and sodium ions. This ionic current may be triggered by extracellular glutamate addition and recorded by an extracellular electrode. Thus, this system may be used as a sensor for gluatmate concentration. Some characteristics of NMDA channels show the high suitability to use this channels as a part of a sensor (single channel conductivity 50 pS; selectivity for cations: $K^+$, $Na^+$ and $Ca^{2+}$; voltage dependency; channel will only open in the presence of glycine; Kandel et al., Neurowissenschaften 236 (1996), Spektrum Verlag).

In an embodiment of the invention a cell which is transfected with receptors for L-glutamate is grown on a chip. A certain amount of L-glutamate is released by flashlight. By this means, the receptor will be opened and an ion current begins to flow. The ion flow may be detected by the electrode. This means that the ion current through the receptor may be triggered by a flashlight.

Figure 1B:
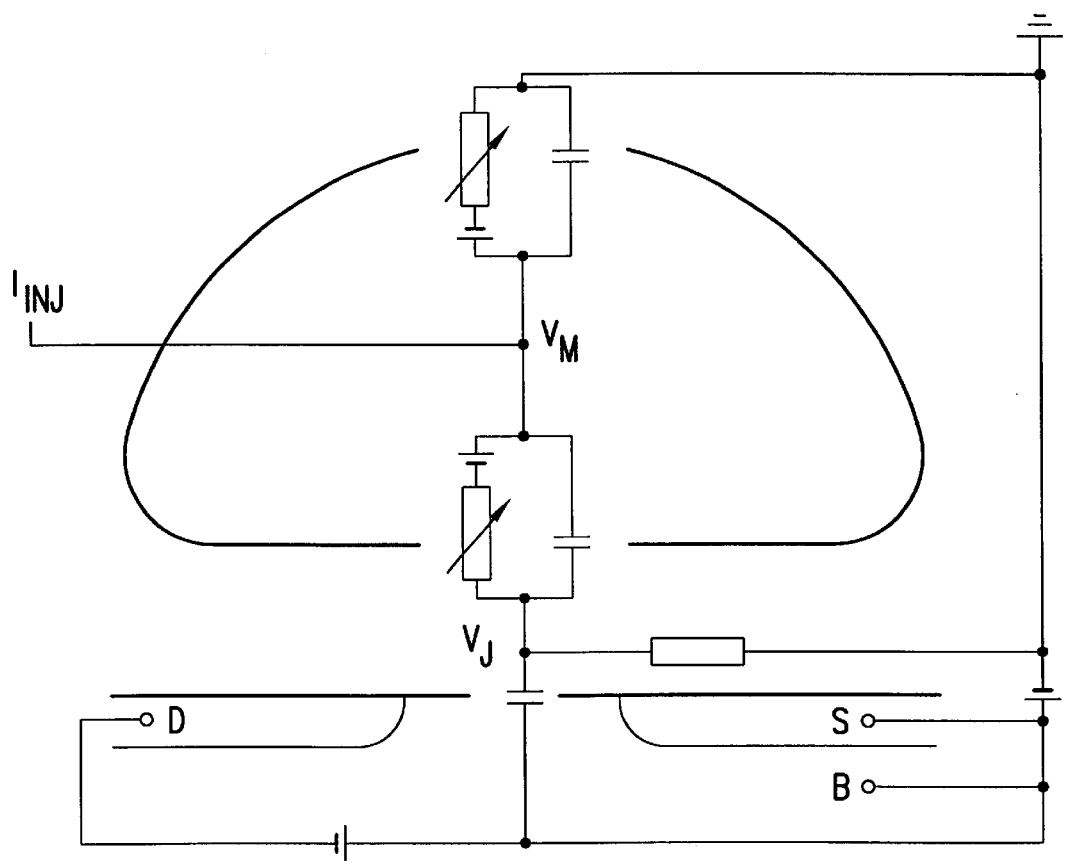

When a cell is attached to the electrode surface, which may be oxidized silicon, other insulated semiconductors or metal, the cell membrane and the electrode surface are separated by a cleft which may be filled with an electrolyte as illustrated in FIG. 1. Thus, a sandwich structure is formed of e.g. silicon, silicon dioxide, cleft, cell membrane and cell interior. The electrode may be integrated on, e.g. embedded in a chip. The chip may comprise further devices such as stimulating spots, transistors etc. Preferably the chip has at least one integrated field-effect transistor comprising at least one source and drain or an electrode as stimulating spot for applying voltages. The potential sensitive electrode, however, may also be a metal electrode which may be integrated on a chip.

The equivalent circuit of the planar core-coat conductor in a cell-silicon junction is shown in FIG. 1$a+b$. Capacitances are assigned to the membrane and to the oxide in the junction. One or several ion conductances in the attached membrane may be driven by Nernst potentials. The extended cleft is represented by an ohmic conductance. The free part of the cell is described by a capacitance and one or several ion conductances, too. The ionic and capacitive currents in the circuit determine the intracellular voltage $V_M$ and the extracellular voltage $V_J$ in the cleft. The voltage $V_J$ in the junction controls the transistor. It plays the same role as the gate-voltage on the metalized gate of a common MOS-FET.

We apply Kirchhoff's law to the node in the junction of FIG. 1$b$, and obtain Eq. 1 for the voltage $V_J$, with the membrane capacitance per unit area $c_M$, the ion conductance $g^1_{JM}$ per unit area of the membrane in the junction, the reversal voltage $V^1_0$ and a cleft conductance $g_J$ per unit area of the junction. The approximation of Eq. 1 is valid for weak coupling, i.e. for small values of $V_J$ and $dV_J/dt$ at a modest electrode capacitance $c_{OX}$.

$$g_J V_J = g^1_{JM}(V_M - V^1_0) + c_M \frac{dV_M}{dt} \tag{1}$$

The properties of the planar core-coat conductor are "squeezed" into the cleft conductance $g_J$ per unit area of the junction according to Eq. 2 with the distance $d_J$ of membrane and substrate, with the specific resistance $\rho_J$ of the electrolyte in the cleft and with the radius $a_J$ of a circular junction.

$$g_J = \frac{5\pi d_J}{\rho_J} \frac{1}{\pi a_J^2} \tag{2}$$

We may eliminate the capacitive current in Eq. 1 by taking into account Kirchhoff's law for the intracellular node of FIG. 1$b$. The capacitive current through the total membrane is balanced by the total ion current through the free and the attached areas of the membrane according to Eq. 3, with the specific conductances $g^1_{FM}$ and $g^1_{JM}$ in the two regions and with the ratio β of the areas of attached and free membrane. Again the approximation of Eq. 3 is valid for weak coupling, i.e. for small values of $V_J$ and $dV_J/dt$.

$$(1+\beta) c_M \frac{dV_M}{dt} = -(g^1_{FM} + \beta g^1_{JM})(V_M - V^1_0) \tag{3}$$

Inserting Eq. 3 into Eq. 1, taking into account Eq. 2, we obtain the coupling relation for an ionoelectronic sensor according to Eq. 4.

$$V_J = \frac{\rho_J a_J^2}{5 d_J} \frac{g^1_{JM} - g^1_{FM}}{1+\beta}(V_M - V_0^1) \quad (4)$$

The relation shows that a large signal on the gate requires:
(i) a small distance $d_J$ of membrane and substrate,
(ii) a large radius $a_J$ of the contact,
(iii) an enhanced or depleted conductance of the receptor channels in the attached membrane with $g^1_{JM}-g^1_{FM} \neq 0$, and
(iv) an electrochemical driving force $V_M-V^1_0$.

Thus, the bioelectronic device of the invention is suitable as a sensor which allows the determination of a change in an environmental parameter as a detectable signal on the electrode and which is suitable as a scientific tool for studying the conformational and functional states of membrane proteins.

Particularly, the environmental parameter is an effector for the receptor component of the ion channel/receptor system. More particulary, the system is used to determine, if a test substance is capable of activating or inhibiting the receptor component of the ion channel/receptor system. The receptor component may be a pharmaceutically relevant target molecule. Thus, the present invention provides a method for contacting a test substance with a bioelectronic device as described above, wherein said bioelectronic device comprises a cell expressing and preferably overexpressing an ion channel/receptor system, wherein a response of the receptor to the test substance is determined by an electric signal in the electrode of the bioelectronic device.

In another embodiment, the bioelectronic device may be used as a sensor to determine the presence or the amount of a substance which acts as an effector to the receptor component of the bioelectronic device.

Further, the invention shall be explained by the following figures and examples:

FIG. 1
a) A schematic picture of an ionoelectronic sensor with a cell on an open field-effect transistor. A thin cleft of electrolyte separates the attached membrane from the silicon dioxide of the silicon chip. A chemical signal in the solution opens receptor channels in the free and in the attached membrane. Ionic current flows through the free and attached membrane, driven by a suitable thermodynamic force. The resulting superposition of ionic and capacitive current throught the attached membrane flows along the narrow cleft and gives rise there to a voltage drop. The change of extracellular voltage in the cleft plays the role of a gate voltage for the open field-effect transistor and modulates the electronic current from source (S) to drain (D) in the silicon chip.

b) Equivalent circuit of the planar core-coat conductor in a cell-transistor junction (point-contact model). The width of the cleft between membrane and chip is blown up. Source (S), drain (D) and bulk silicon (B) are kept at bias voltages with respect to the bath. The intracellular voltage $V_M$ and the extracellular voltage $V_J$ depend on the capacities of the attached and free membrane, on one or several ion conductances—driven by Nernst-type batteries—, on the stray capacitance of the chip and on the conductance of the cleft. A substance in the bath which opens ion channels affects conductances in the attached and free membrane. The resulting change of the voltage $V_J$ is detected by the transistor. An injection current $I_{INJ}$ can be applied by an impaled or fused micropipette.

Figure 2:
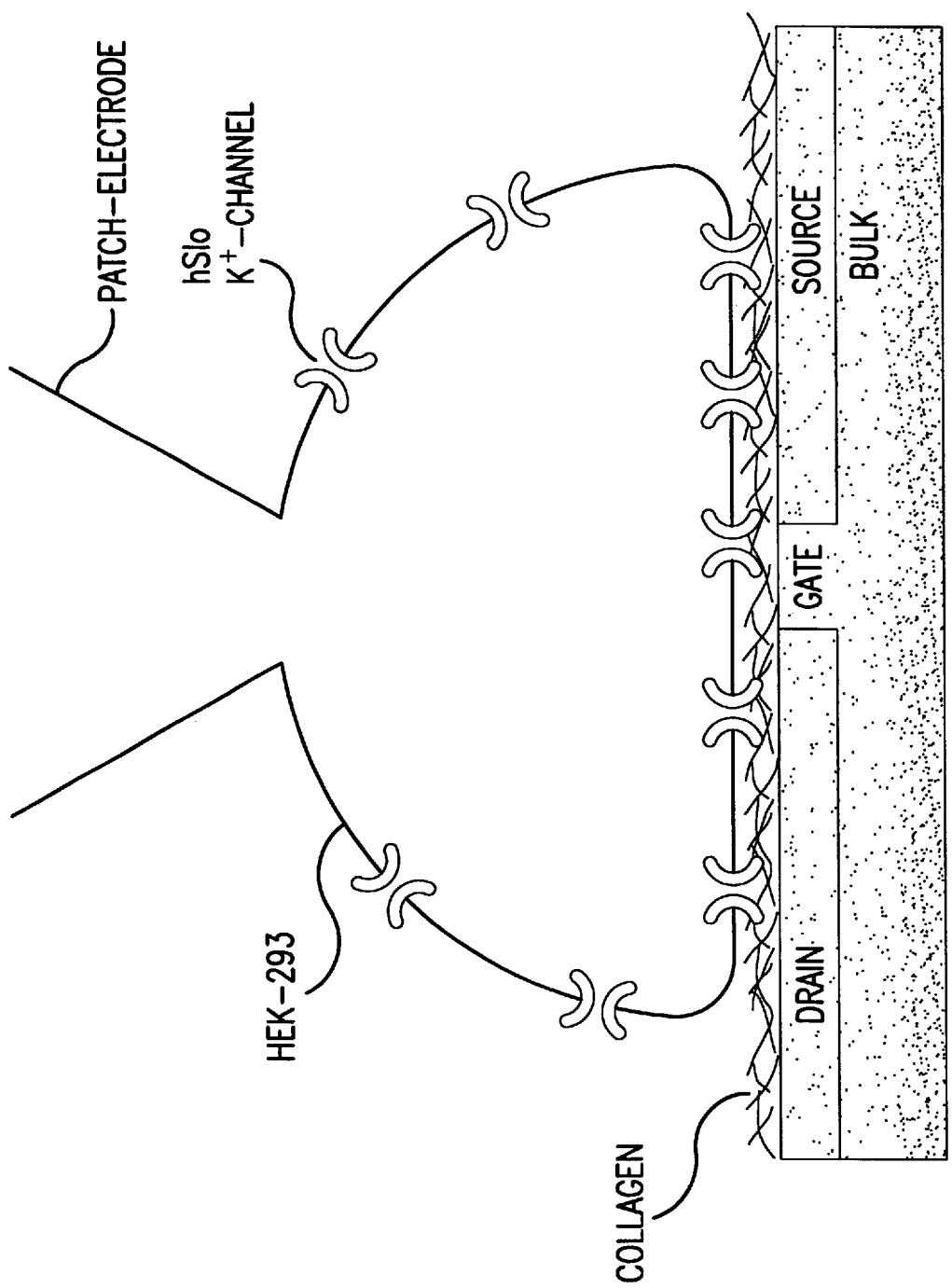

FIG. 2
A schematic picture of an embodiment of the present invention. The voltage and calcium dependent human slowpoke (hSlo) potassium channel was expressed in HEK 293 cells. Transfected cells on a gate are contacted with a patch pipette in a whole cell configuration. In the voltage clamp modus the total voltage dependent potassium current of the cell is detected. Simultaneously, the extracellular voltage between cell and gate caused by the local potassium current is determined.

EXAMPLES

1. Materials and Methods 1.1 Cells and Plasmids

HEK 293 cells were cultivated in plastic dishes (Becton Dickinson, Plymouth, UK, No.110L7807P) in growth medium consisting of Dulbecco's modified Eagle's medium (DMEM, No. 074-02100 A; Gibco Eggenstein, Germany) with 4.5 mg/ml glucose, 10% heat-inactivated fetal bovine serum (S181; Seromed; Berlin, Germany), 3.7 mg/ml $NaHCO_3$ (S5761 Sigma), 2 nM L-gutamine (G2150; Sigma), 25 U/ml penicillin and 25 U/ml streptomycin (043-05140; Gibco).

The cells were transfected with two plasmids: the hSLo α-subunit construct in the plasmid pcDNA3, which was obtained by cloning the nucleic acids encoding the α-subunit of the human slowpoke potassium channel in the vector pcDNA3 (Invitrogen) (Tseng-Crank J., Foster C. D., Krause J. D., Mertz R., Godinoot N., DiChiara T. J., Reinhart P. H., "Cloning, Expression and Distribution of Functionally Distinct $Ca^{2+}$ Activated $K^+$Channel Isoforms from Human Brain", Neuron, 13, 1315–1330, 1994) and the pEGFP-CI Plasmid (Clontech, Palo Alto, Calif., USA), which contains the GFP gene and serves as a control for successful transfection.

The cells were transfected with the calcium phosphate transfection technique 1 day after replating by coprecipitation with a solution containing both plasmid DNAs.

1.2 Cell Culture on the Substrate

The transfected cells were cultivated on a collagen-coated silicon chip having 96 field-effect transistors. Green fluorescent cells located on a gate were used for patch-clamp determinations.

2. Results

Transfected cells located on a gate were contacted with a patch-clamp in whole-cell configuration. The total voltage dependent potassium current in the cell was determined under voltage-clamp. Further, the change of the extracellular potential caused by the local potassium current between cell and gate was determined. This local potassium current was high enough that transistor signals could be observed without signal averaging.

The specific voltage dependent potassium conductivity in the area of adhesion (area of contact between cell and chip) was obtained by calibrating the extracellular voltage in the junction with the specific cell-chip-contact conductivity and dividing through the distance of voltage and reverse potential. It was found that the functionality of the hSlo potassium channel is not influenced by the adhesion. Thus, a functional bioelectronic device for determining the influence of environmental parameters on an ion channel/receptor system is provided.

What is claimed is:

1. A bioelectronic device comprising
   (a) a cell which expresses an ion channel/receptor system wherein said ion channel/receptor system comprises an ion channel component that mediates an ion current through a cell membrane and a receptor component; and
   (b) an extracellular potential-sensitive electrode wherein the cell is in operative contact with said electrode,
   wherein the cell has been manipulated to overexpress said ion channel/receptor system.

2. The device of claim 1, wherein said cell is a eukaryotic cell.

3. The device of claim 1
   wherein the cell is transfected with nucleic acid molecules encoding components of the ion channnel/receptor system.

4. The device of claim 1, wherein said ion channel is selected from voltage-gated ion channel, ligand-gated ion channels, mechanically-gated ion channels or combinations thereof.

5. The device of claim 1, wherein the potential-sensitive electrode is located on a chip.

6. The device of claim 5
   wherein the chip has at least one integrated field-effect transistor comprising at least one source and a drain or an electrode as stimulating spot for applying voltages.

7. The device of claim 6
   wherein the cell is in operative contact with at least one gate region between a source and a drain or stimulating spot.

8. The device of claim 1, wherein the potential-sensitive electrode is a metal-electrode.

9. The device of claim 1, wherein a voltage drop is measured across the ion channel or the membrane.

10. The device of claim 1, wherein the receptor component in response to a change in stimuli causes the ion channel component to change the ion current.

11. A bioelectronic device comprising
    (a) a cell which expresses an ion channel/receptor system wherein said ion channel/receptor system comprises an ion channel component that mediates an ion current through a cell membrane and a receptor component; and
    (b) an extracellular planar potential-sensitive electrode wherein the cell is in operative contact with said electrode,
    wherein the ion channel is the potassium channel hSlo.

12. A method of using a bioelectric device, the method comprising:
    providing the bioelectric device of claim 1; and
    using the bioelectric device to detect changes in the ion channel current with an extracellular potential-sensitive electrode.

13. The method of claim 12, wherein a change in an environmental parameter is sensed as a detectable signal on the electrode.

14. The method of claim 12 wherein the environmental parameter is an effector for the receptor component of the ion channel/receptor system.

15. The method of claim 14 further comprising:
    determining if a test substance activates or inhibits the receptor component.

16. The device of claim 11 wherein said cell is a eukaryotic cell.

17. The device of claim 11, wherein the potential-sensitive electrode is located on a chip.

18. The device of claim 17, wherein the chip has at least one integrated field effect transistor comprising at least one source and a drain or an electrode as a stimulating spot for applying voltages.

19. The device of claim 18, wherein the cell is in operative contact with at least one gate region between a source and a drain or stimulating spot.

20. The device of claim 11, wherein the potential-sensitive electrode is a metal-electrode.

21. The device of claim 11, wherein the potential-sensitive electrode is a transistor.

22. A bioelectronic device comprising
    (a) a cell which expresses an ion channel/receptor system wherein said ion channel/receptor system comprises an ion channel component that mediates an ion current through a cell membrane and a receptor component; and
    (b) an extracellular planar potential-sensitive electrode wherein the cell is in operative contact with said electrode,
    wherein the ion channel is the ionotropic glutamate receptor NMDA.

23. The device of claim 22 wherein said cell is a eukaryotic cell.

24. The device of claim 22, wherein the potential-sensitive electrode is located on a chip.

25. The device of claim 24, wherein the chip has at least one integrated field effect transistor comprising at least one source and a drain or an electrode as a stimulating spot for applying voltages.

26. The device of claim 25, wherein the cell is in operative contact with at least one gate region between a source and a drain or stimulating spot.

27. The device of claim 22, wherein the potential-sensitive electrode is a metal-electrode.

28. The device of claim 22, wherein the potential-sensitive electrode is a transistor.

* * * * *